(12) United States Patent
Floberg et al.

(10) Patent No.: US 9,199,410 B2
(45) Date of Patent: Dec. 1, 2015

(54) METHOD OF FORMING AN ELASTIC LAMINATE

(75) Inventors: Per Floberg, Lindome (SE); Mats Kinderdal, Molnlycke (SE); Inge Gabrielii, Kallered (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 0 days.

(21) Appl. No.: 14/129,717

(22) PCT Filed: Jun. 30, 2011

(86) PCT No.: PCT/SE2011/050878
§ 371 (c)(1),
(2), (4) Date: Dec. 27, 2013

(87) PCT Pub. No.: WO2013/002691
PCT Pub. Date: Jan. 3, 2013

(65) Prior Publication Data
US 2014/0130956 A1  May 15, 2014

(51) Int. Cl.
*A61F 13/15* (2006.01)
*B29C 55/06* (2006.01)
(Continued)

(52) U.S. Cl.
CPC ......... *B29C 55/065* (2013.01); *A61F 13/15593* (2013.01); *A61F 13/15699* (2013.01); *A61F 13/15731* (2013.01); *A61F 13/4902* (2013.01); *B29C 65/08* (2013.01); *B32B 3/266* (2013.01); *B32B 5/022* (2013.01); *B32B 7/045* (2013.01); *B32B 7/12* (2013.01); *B32B 27/302* (2013.01);
(Continued)

(58) Field of Classification Search
CPC .................. A61F 13/15577; A61F 13/4902
USPC ................... 156/163, 164, 229, 73.1
See application file for complete search history.

(56) References Cited

U.S. PATENT DOCUMENTS 4,720,415 A * 1/1988 Vander Wielen et al. ...... 156/163
5,376,198 A * 12/1994 Fahrenkrug et al. .......... 156/164
(Continued)

FOREIGN PATENT DOCUMENTS

EP   1 329 303 A1   7/2003
JP   2009-539423   11/2009
(Continued)

OTHER PUBLICATIONS

Extended European Search Report dates Nov. 25, 2014 issued in corresponding European Patent Application No. 11868444.8 (6 pages).

(Continued)

*Primary Examiner* — Jeff Aftergut
(74) *Attorney, Agent, or Firm* — Drinker Biddle & Reath LLP

(57) ABSTRACT

A method of forming an elastic laminate including at least one elastic film and least two nonwoven webs laminated to each of the sides of the elastic film. The elastic film is fed in a machine direction towards a bonding station. The elastic film is stretched in the machine direction at a stretch ratio from 1.5 to 8 times of its original length, thereby forming a stretched film and the stretched film and said at least two nonwoven webs are laminated in the bonding station. The elastic film is stretched in at least two stretching steps before laminating it with the at least two nonwoven webs, wherein between 5 and 25% of the total stretching occurs in the last stretching step before lamination in the bonding station.

10 Claims, 2 Drawing Sheets

(51) Int. Cl.
*B29C 65/08* (2006.01)
*B32B 5/02* (2006.01)
*B32B 7/04* (2006.01)
*B32B 7/12* (2006.01)
*B32B 27/30* (2006.01)
*B32B 3/26* (2006.01)
*A61F 13/49* (2006.01)
*B32B 37/14* (2006.01)

(52) U.S. Cl.
CPC ..... *B32B 37/144* (2013.01); *A61F 2013/15869* (2013.01); *A61F 2013/15991* (2013.01); *B32B 2262/0253* (2013.01); *B32B 2307/51* (2013.01); *B32B 2307/514* (2013.01); *B32B 2555/02* (2013.01)

(56) References Cited

U.S. PATENT DOCUMENTS

| | | | |
|---|---|---|---|
| 6,179,939 B1 * | 1/2001 | Jones et al. | 156/164 |
| 6,627,564 B1 | 9/2003 | Morman et al. | |
| 7,803,244 B2 * | 9/2010 | Siqueira et al. | 156/229 |
| 2002/0086602 A1 | 7/2002 | Friderich et al. | |
| 2002/0119722 A1 | 8/2002 | Welch et al. | |
| 2004/0005834 A1 | 1/2004 | Zhou et al. | |
| 2004/0121683 A1 | 6/2004 | Jordan et al. | |
| 2006/0148358 A1 | 7/2006 | Hall et al. | |
| 2008/0003910 A1 | 1/2008 | Hughes et al. | |
| 2008/0095978 A1 | 4/2008 | Siqueira et al. | |
| 2009/0099542 A1 | 4/2009 | Thomas et al. | |
| 2009/0299314 A1 * | 12/2009 | Middlesworth et al. | 156/229 |
| 2010/0139846 A1 | 6/2010 | Nordang | |

FOREIGN PATENT DOCUMENTS

| | | |
|---|---|---|
| RU | 2156693 C2 | 9/2000 |
| RU | 2293659 C2 | 2/2007 |
| WO | WO-01/32116 A1 | 5/2001 |
| WO | WO 02/22343 A1 | 3/2002 |
| WO | WO-2005/021262 A1 | 3/2005 |
| WO | WO 2005/023544 | 3/2005 |
| WO | WO 2007/146149 A2 | 12/2007 |
| WO | WO-2008/026106 A2 | 3/2008 |
| WO | WO-2009/138887 A2 | 11/2009 |
| WO | WO-2012/036599 A1 | 3/2012 |

OTHER PUBLICATIONS

Notice of Reasons for Rejection mailed Jun. 22, 2015 in Japanese Patent Application No. 2014-518484 (with English translation) (7 pages).

English-language translation of Russian Decision on Grant dated Jul. 28, 2015 issued in corresponding Russian patent application No. 2014103033 (4 pages).

* cited by examiner

METHOD OF FORMING AN ELASTIC LAMINATE

CROSS-REFERENCE TO PRIOR APPLICATION

This application is a §371 National Stage Application of PCT International Application No. PCT/SE2011/050878 filed Jun. 30, 2011, which is incorporated herein in its entirety.

TECHNICAL FIELD

The present disclosure refers to a method of forming an elastic laminate including at least one elastic film and at least two nonwoven webs. The elastic film and the nonwoven webs are laminated while the elastic film is kept in a stretched condition.

BACKGROUND

Elastic laminate materials are commonly incorporated in absorbent articles, especially pant-like absorbent articles such as pant diapers, sanitary pants, incontinence pants, and the like. Such articles include an absorbent unit arranged in a pant-shaped chassis and are worn in the manner of a pair of underpants. Elastic laminate materials may be incorporated as part of front and/or rear body panels and/or as elastic side panels in a pant-like absorbent article.

If the elastic film is in a stretched condition in a machine direction (MD) during bonding to the at least one nonwoven layer, the nonwoven layer can gather between the bonding sites in a relaxed condition and thus make the laminate material elastically stretchable in said machine direction. Such bonding by melt fusing, for example accomplished by thermal bonding or ultrasonic welding, may result in that apertures are formed in the film in the bond sites or adjacent thereto. This will make the elastic film and the laminate breathable, which is advantageous and increases wearer comfort in an absorbent article.

WO 2008/026106 discloses a breathable elastic laminate suitable to be incorporated in an absorbent article. The laminate includes an elastic film and a nonwoven web bonded together by melt fusing in a plurality of bonding sites while the film is in a stretched condition. Apertures are formed in the film in the bonding sites concurrently with melt fusing without substantially softening the polymer material of the nonwoven web.

WO 2009/138887 discloses a method for forming a latent elastic composite from a multilayered elastic film laminated to a nonwoven facing. The elastic multilayered film is stretched in the machine direction at a stretch ratio from 1.5 to 7.0, thereby forming a stretched elastic film. The stretched elastic film is allowed to relax to achieve a relaxation percentage of at least 10% and is then laminated to the nonwoven web facing in the relaxed condition.

US 2010/0139846 discloses a method for bonding elastomeric high loft substrates wherein the elastomeric high loft substrates are introduced into the bonding station in a stretched state.

The international application PCT/SE2010/050986 discloses an elastic laminate including at least one elastic film layer and at least one nonwoven layer. The elastic film and the nonwoven layer are bonded together in a bonding pattern including a plurality of bonding elements in which the film and nonwoven are fused together. The elastic film is held in a stretched state during bonding. Apertures are formed in the elastic film in close vicinity to the bonding elements caused by rupture of the film as a result by stretching. These apertures make the film breathable.

There is still a need for a method of manufacturing an elastic laminate in which the process for stretching the elastic film prior to bonding to the nonwoven web is controlled so that bonding will occur in a controlled manner. This is especially important when the stretched elastic film is bonded to the nonwoven web(s) by melt fusing in a bonding pattern, wherein apertures are formed in the film in or in close vicinity to the bonding elements.

SUMMARY

Disclosed herein is a method of forming an elastic laminate. The elastic laminate includes at least one elastic film and at least one nonwoven web. The method includes: providing an elastic film and feeding it in a machine direction towards a lamination station; stretching said elastic film in the machine direction at a stretch ratio from 1.5 to 8 times of its original length, thereby forming a stretched film; and laminating the stretched film and the at least two nonwoven webs.

The elastic film is stretched in at least two stretching steps before laminating it with said at least two nonwoven webs, and between 5 and 25% of the total stretching occurs in the last stretching step before lamination.

The elastic film and the at least two nonwoven webs may be laminated by thermal bonding or ultrasonic welding in a bonding pattern including a plurality of bonding elements.

Apertures may be formed in the elastic film at or in close vicinity of at least some of the bonding elements, said apertures being caused by rupture of the elastic film as a result by stretching.

The elastic film may pass over at least two stretch rolls before entering the bonding station wherein the last stretching step takes place between the last stretch roll and the bonding station.

The elastic film may pass over at least three stretch rolls before entering the bonding station.

The elastic film may be stretched in at least three steps before entering the bonding station.

The free length between adjacent stretch rolls may be between 10 and 150 mm.

The basis weight of the laminate may be between 40 and 100 $g/m^2$ and the basis weight of the elastic film may be between 20 and 60 $g/m^2$.

DEFINITIONS

The term "machine direction" or "MD" refers to the direction in which a material, in the present case the elastic laminate, is produced. The term "cross-machine direction" or "CD" refers to the direction perpendicular to the machine direction.

The term "elastic" or "elastomeric" refers to a material that upon an application of a stretching force is stretchable in at least one direction, for example in the MD, and which upon release of the stretching force contracts, i.e. returns to its original dimension. An elastic material is defined as a material having a permanent elongation after relaxation of less than 10% after the material has been subjected to an elongation of 30%. An elongation of 30% means an elongation to a length that is 30% longer than the initial length of the sample. The material is tested in a tensile tester, Lloyd LRX, as described in the "Elasticity test" below.

The term "stretch ratio" is defined as the length of the stretched film divided by its length before stretching.

BRIEF DESCRIPTION OF THE DRAWINGS

Embodiments of the invention will be described below with reference to the accompanying drawings.

DETAILED DESCRIPTION OF PREFERRED EMBODIMENTS

An elastic laminate material 10 includes at least one elastic film 11 and at least two fibrous nonwoven layers 12, 13 having the elastic film layer there between. Suitable nonwoven materials and elastic films are selected depending on the intended use of the elastic laminate. For use in an absorbent article suitable materials are given below.

Figure 1:
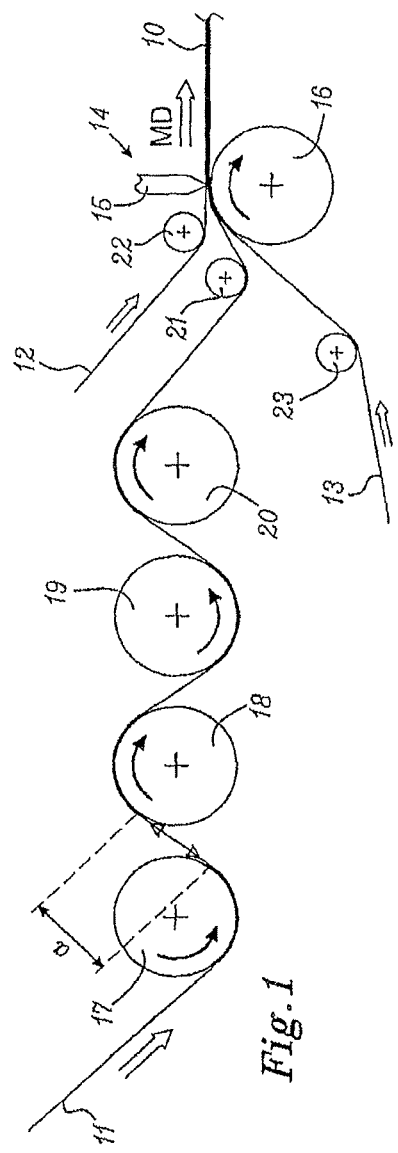
FIG. 1 schematically illustrates a method for forming an elastic laminate according to one embodiment of the present invention.

In the method illustrated in FIG. 1 the layers 11, 12 and 13 are bonded together in a bonding station 14 with a bonding pattern including a plurality of bonding elements in which the elastic film 11 and the nonwoven webs 12 and 13 are fused together. The bonding technique can be thermal point bonding, ultrasonic bonding or the like. Thermal point bonding employs a nip formed between two rolls, at least one being patterned. One or both rolls are heated. Ultrasonic bonding employs a bonding nip formed between an ultrasonic horn 15 and a patterned roll 16. In both techniques, the patterned roll 16 includes a plurality of raised bonding elements to bond the film to the nonwoven layer(s) in a bonding pattern formed by the raised bonding elements.

The elastic film 11 is in a stretched condition during bonding, said stretching is in the machine direction (MD) of the laminate. In certain embodiments, the degree of stretching is at least 1.5 times its original length, or in the range 3 to 8 times its original length. The stretching takes place in at least two stretching steps as will be described more in detail below.

After relaxation of the film 11 the nonwoven layer(s) 12, 13 can gather between the bonding sites and thus make the laminate material 10 elastically stretchable in said machine direction.

The elastic film 11 passes over a number of stretch rolls 17, 18, 19 and 20 before it is laminated to the nonwoven layers 12 and 13 in the bonding station 14 formed of the ultrasonic horn 15 and the patterned roll 16. The number of stretch rolls is four in the embodiment shown in FIG. 1. The number of stretch rolls should be two or more and may be three, four, five, six or more. The stretch rolls have a smooth high friction surface, for example a polymer coating. One example of a suitable high friction polymer coating is PlasmaCoat 30301/4001F-12.

The elastic film 11 is stretched between two or more of the stretch rolls, for example between the rolls 17 and 18, by running the roll 18 at a higher peripheral speed than the roll 17. According to embodiments of the invention the elastic film 11 is stretched in at least two stretching steps. The last stretching step takes place between the last stretch roll 20 and the bonding station 14. Between 5 and 25% of the total stretching of the elastic film takes place in this last stretching step. Thus between 75 and 95% of the total stretching of the elastic film takes place in one or more steps between the stretch rolls 17, 18, 19, and 20.

A guide roll 21 is arranged between the last stretch roll 20 and the bonding station 14 in order to adjust the wrap angle of the elastic film 11 with respect to the patterned roll 15. Guide rolls 22 and 23 are also provided for the nonwoven webs 12 and 13 before the bonding station 14.

It is desired that the so called "necking" of the elastic film 11 is minimized, wherein "necking" refers to constriction of the film in the width direction (CD) during stretching. Necking is prevented or reduced by minimizing the distance between the stretch rolls 17, 18, 19, and 20. The distance between adjacent stretch rolls may be measured as the free length, a, between the rolls, i.e. the distance between the point where the film leaves one roll and where the film comes in contact with the next roll. This free length, a, may be between 10 and 150 mm in order to minimize necking of the film.

Figure 2:
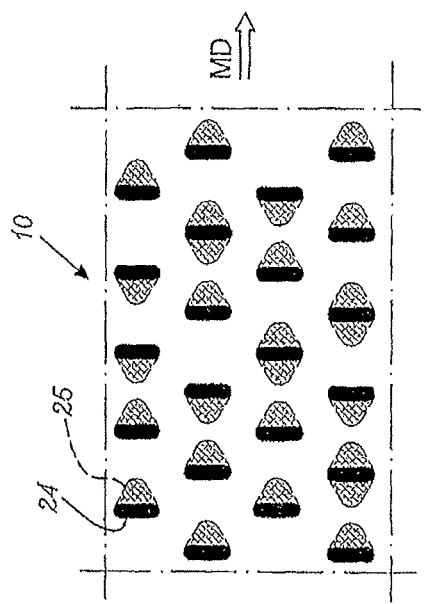
FIG. 2 shows schematically an example of a bonding pattern for bonding the elastic laminate.

Depending on the choice of bonding elements 24 in the bonding pattern bonding together the nonwoven webs 12, 13 and the elastic film 11 apertures 25 may be formed in the elastic film in close vicinity of at least some of the bonding elements 24. This is illustrated in FIG. 2. These apertures 25 are formed by rupture of the elastic film as a result of stretching. These apertures 25 may be located outside the area of the respective bonding element 24 and are formed due to tensions in the film in the area in close vicinity to the bonding elements. "In close vicinity" means that the apertures extend from the perimeter of the respective bonding element. The apertures extend substantially in the MD and may be located in front of and/or behind the respective bonding element 24. The apertures render the elastic laminate 10 breathable.

This is described more in detail in the international application PCT/SE2010/050986 in which examples of bonding patterns are given which will provide the formation of apertures in the film.

The above described method of stretching the elastic film in two or more steps, wherein the last stretching step takes place between the last stretch roll and the bonding station, makes the elastic film to open up immediately before the bonding, resulting in an improved control of the bonding and the characteristics of the elastic laminate produced. The film is more sensitive during stretching, which makes it "open up" during bonding. This is especially important when apertures are formed in the film during bonding and the multi-step stretching will improve the control of the formation of apertures and thus the breathability of the laminate.

The elastic laminate may be used in an absorbent article. The term "absorbent article" refers to products that are placed against the skin of the wearer to absorb and contain body exudates, like urine, faeces and menstrual fluid. Such absorbent articles are often disposable, which means articles that are not intended to be laundered or otherwise restored or reused as an absorbent article after use. The absorbent article including the elastic laminate can be a pant-type absorbent article such as a pant diaper, sanitary pant or incontinence pant.

Figure 3:
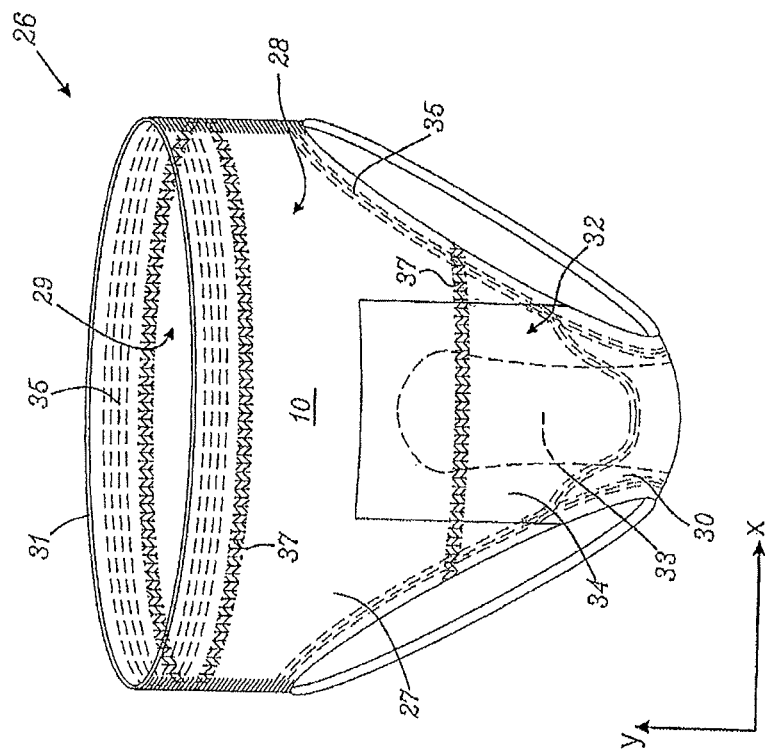
FIG. 3 shows an example of a pant-type absorbent article having elastic body panels.

FIG. 3 shows an embodiment of a pant-type absorbent article 26 for an infant or an incontinent adult or a sanitary pant. Said pant article includes a chassis 27 including a front panel 28, a back panel 29, a crotch portion 30 and an elastic waistband 31. A core region 32 including an absorbent core 33 is located at least in the crotch portion 30 of the article and extends a certain distance into the front 28 and back panels 29. The crotch portion 30 is herewith defined as the narrow part of the article intended to be worn in the wearer's crotch between the legs. In a further embodiment (not shown) the front and back panels are separated from each other and the core region, including the absorbent core, bridges the gap between the front and back panels.

The core region 32 further includes a liquid impervious backsheet 34 underlying the absorbent core 33 and a liquid pervious topsheet (not shown) on the wearer facing side of the absorbent core. The absorbent core, backsheet and topsheet may be of materials commonly used in absorbent articles.

The article has a longitudinal direction y and a transverse direction x.

According to an embodiment, the surface area of the absorbent core 30 amounts to no more than 30% of the total surface area of the article, or no more than 20%, as measured in a flat state of the article. The term "flat state" herein means in an opened untensioned state in which the side seams are opened and in which any tensioned elastic members have been deactivated.

The elastic laminate 10 may cover the entire article, including the core region 32 and the entire chassis region 27. According to another embodiment, a substantial part of the crotch portion 30 of the article is free from the elastic web material 10. A "substantial part" used herein refers to at least 50%, or at least 75%. Also the waist region of the chassis region may be free from the elastic laminate 10 and may include a separate elastic waistband 31. The elastic waistband 31 includes a nonwoven material that is elasticized by elastic members 35, such as elastic threads, contractably affixed between material layers, such as nonwoven materials. Such elastic members 35 may also be arranged around the leg openings of the article. Ultrasonic welds 37, glue strings or the like, join the elastic laminate 10 to the elastic waistband 31.

A nonwoven material may be arranged on the garment-facing side of the liquid-impervious backsheet 34 in the crotch portion of the article. The nonwoven material is joined to the elastic laminate 10 by means of ultrasonic welds 37, glue strings or the like.

The elastic laminate 10 can be arranged as an outside coversheet material as well as inner coversheet material over at least a substantial part of the front region 28 of the chassis 27, which during use is intended to be applied against the stomach of the wearer, except for the waist region. A "substantial part" used herein means at least 50% of the surface area, or at least 75%, of the surface area of the front region of the chassis. In other embodiments, the elastic laminate 10 is arranged as an outside coversheet material as well as inner coversheet material over both the front 28 and back regions 29 of the chassis 27. Thus no additional backsheet or topsheet materials are required and the elastic web material constitutes the sole component in these parts of the chassis 27. In at least 20%, at least 25%, at least 30%, or at least 40% of the total surface area of the article, as seen in a flat state, as referred to above, the elastic laminate 10 constitutes the sole component of the chassis.

The outer coversheet covering the front and back panels 28 and 29 of the chassis 27 includes an elastic laminate material 10, which is elastic at least in the transverse x-direction of the article. The elasticity in the x-direction should be at least 30%, at least 50%, or at least 70%, as measured by the Elasticity test specified below. The transverse x-direction of the article herewith corresponds to the MD of the elastic laminate described above.

For an elastic laminate used as a front 28 and/or back panel 29 in a pant-type absorbent article the laminate includes at least three layers, viz. first and second outer nonwoven layers 12, 13, which are chosen so that they, in combination with the inner elastic film layer 11, give the elastic laminate 10 high resistance to puncture, in order to prevent penetration by finger nails for example. They also provide a soft and cloth-like feel to the laminate. Examples of suitable materials are carded webs and spunbond materials. The basis weight of the fibrous material layers should be between 10 and 35 $g/m^2$, between 12 and 30 $g/m^2$, or between 13 and 25 $g/m^2$. Examples of suitable polymers used in the fibrous materials are polyethylene, polyesters, polypropylene and other polyolefin homopolymers and copolymers. Natural fibres, for example cotton, may also be used as long as they provide the required properties. A mixture of polymers can contribute to a higher flexibility of the nonwoven layer, and through this, give the nonwoven material a higher elongation at maximum load. A mixture of polyethylene and polypropylene polymers has proved to provide good results in this respect. A mixture of fibers of different polymers is also possible. The nonwoven layers 12, 13 should be chosen so that the tensile strength of the laminate will be sufficient for the intended purpose.

The elastic film 11 can have a basis weight between 20 and 80 $g/m^2$, or between 20 and 60 $g/m^2$. The elastic film 11 may be of any suitable elastic polymer, natural or synthetic. Some examples of suitable materials for the elastic film are low crystallinity polyethylenes, metallocene-catalyzed low crystallinity polyethylene, ethylene vinyl acetate copolymers (EVA), polyurethane, polyisoprene, butadiene-styrene copolymers, styrene block copolymers, such as styrene/isoprene/styrene (SIS), styrene/butadiene/styrene (SBS), or styrene/ethylene-butadiene/styrene block copolymer. Blends of these polymers may also be used as well as other modifying elastomeric or non-elastomeric materials. One example of a suitable elastic film is a three-layer elastomeric film of PE-SEBS-PE.

The total basis weight of the elastic laminate 10 can be between 40 and 100 $g/m^2$, or not more than 90 $g/m^2$.

Figure 4:
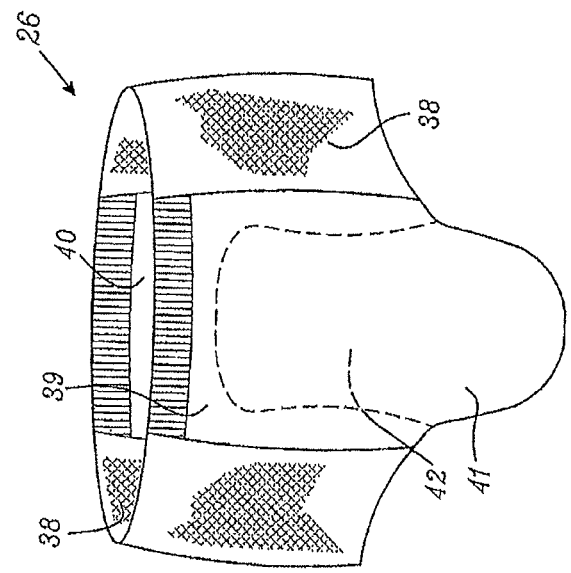
FIG. 4 shows another example of a pant-type absorbent article having elastic side panels.

Although the elastic laminate 10 can be used in pant-type absorbent articles, in which the elastic laminate extends all the way between the side seams of the article, in at least one of the front and back panels, it may also be used to form for example elastic side panels in an absorbent article. FIG. 4 illustrates a pant-type absorbent article including elastic side panels 38. The article further includes a front body panel 39 and a back body panel 40 and a crotch portion 41. The front and back body panels as well as the crotch portion are generally comprised of a liquid impermeable backsheet, a liquid permeable topsheet and an absorbent core 42 located between the backsheet and the topsheet. The absorbent core, backsheet and topsheet may be of materials commonly used in absorbent articles. The backsheet may further include a layer of nonwoven material laminated to a film layer, in which case there is provided a more cloth-like and garment-like feel than is typically obtained with a film backsheet only.

The elastically extensible side panels 38 are provided to ensure more comfortable and contouring fit. The elastic side panels 38 or at least parts thereof may include the elastic laminate 10. Leg elastics and waist elastic regions may also be provided to enhance the fit around the legs and waist, respectively.

TEST METHODS

Elasticity Test

The method measures how an elastic material behaves at repeated load and unload cycles. The sample is stretched to a predetermined elongation and a cyclic movement between 0 and said predetermined elongation is performed. Desired load and unload forces are recorded. The permanent, i.e. remaining, elongation of the relaxed material is measured.

A tensile tester, Lloyd LRX, able to perform cyclic movements and equipped with a printer/plotter or software presentation is used. The sample is prepared by cutting it to a width of 25.4 mm and a length that is 50 mm longer than the distance between the clamps in the tensile tester.

The tensile tester is calibrated according to the apparatus instructions. The parameters needed for the test (load and unload forces) are adjusted to:

Crosshead speed: 500 mm/min
Clamp distance: 50 mm
Preload: 0.05 N

The sample is conditioned at least 4 h in 50% RH±5% RH and 23° C.±1° C. and is placed in the clamps according to the marks and it is made sure that the sample is centred and fastened perpendicularly in the clamps. The tensile tester is started and three cycles between 0 and the predetermined elongation, equal to the highest defined $1^{st}$ load, are performed. Before the last cycle, the sample is relaxed for 1 minute, then the permanent elongation is measured by stretching the sample until a force of 0.1 N is detected and the elongation is read.

An elastic material is defined as a material having a permanent elongation after relaxation of less than 10% after the material has been subjected to an elongation of 30%. An elongation of 30% means an elongation to a length that is 30% longer than the initial length of the sample. Thus a material having an elasticity of at least 30% is defined as that the material should have a permanent relaxation after elongation of less than 10% after being exerted to an elongation of 30% in the tensile tester above. A material having an elasticity of at least 50% is defined as that the material should have a permanent relaxation after elongation of less than 10% after being exerted to an elongation of 50% in the tensile tester above, etc.

A non-elastic material has a permanent elongation after relaxation of more than 10% after having been subjected to an elongation of 30%.

EXAMPLE

An elastic laminate comprising an elastic film and two nonwoven layers laminated to each side of the elastic film was produced. The elastic film was a 30 gsm multilayer film from Berry Plastics having a styrene based core layer and polyolefin skin layers. One nonwoven layer was a polypropylene spunbond nonwoven from Freudenberg with the code LS 4516 (white), grammage 16 gsm, titre 1.6-1.8 dtex, and the other nonwoven layer was a polypropylene spunbond nonwoven from Freudenberg with the code Lutrasil 0519 XF, grammage 19 gsm, titre 1.6-1.8 dtex.

The elastic film and the nonwoven layers were laminated by ultrasonic welding in a bonding pattern comprising a plurality of bonding elements in which the elastic film and the nonwoven webs were fused together. The bonding pattern was as defined in PCT/SE2010/050986. The elastic film was stretched in the machine direction at a stretch ratio of 4.5 times of its original length in two stretching steps, wherein 12% of the stretching occurred in the last stretching step immediately before lamination as described above. The stretched film and the nonwoven webs were laminated in the stretched condition of the film. Apertures were formed in the film in close vicinity of the bonding elements caused by rupture of the elastic film as a result by stretching as described above. The elastic laminate that was produced is breathable having an average breathability higher than 12 $m^3/m^2$·min at 200 Pa.

The invention claimed is:

1. A method of forming an elastic laminate comprising at least one elastic film and at least two nonwoven webs laminated to each of the sides of the elastic film, the method comprising:
   providing an elastic film and feeding it in a machine direction towards a bonding station;
   stretching said elastic film in the machine direction in at least two stretching steps to a total stretch ratio from 1.5 to 8 times of its original length, wherein said elastic film passes over at least two stretch rolls before entering said bonding station, wherein between 5 and 25% of the total stretching in the machine direction occurs in the last stretching step, which takes place between the last stretch roll and said bonding station, and wherein the percentage of the total stretching occurring in the last step is different from the percentage of at least one other stretching step, thereby forming a stretched film;
   laminating the stretched film and said at least two nonwoven webs in said bonding station by thermal bonding or ultrasonic welding in a bonding pattern comprising a plurality of bonding elements; and
   forming apertures in said elastic film at or in close vicinity of at least some of the bonding elements, said apertures being formed by rupture of said elastic film as a result of the stretching and laminating steps.

2. The method as claimed in claim 1, wherein said elastic film passes over at least three stretch rolls before entering said bonding station.

3. The method as claimed in claim 2, wherein said elastic film is stretched in at least three steps before entering said bonding station.

4. The method as claimed in claim 1, wherein the free length between adjacent stretch rolls is between 10 and 150 mm.

5. The method as claimed in claim 1, wherein the basis weight of the laminate is between 40 and 100 $g/m^2$ and the basis weight of the elastic film is between 20 and 60 $g/m^2$.

6. A method of forming an elastic laminate comprising at least one elastic film and at least two nonwoven webs laminated to each of the sides of the elastic film, the method comprising:
   providing an elastic film and feeding it in a machine direction towards a bonding station;
   stretching said elastic film in the machine direction in at least two stretching steps to a total stretch ratio from 1.5 to 8 times of its original length, wherein said elastic film passes over at least two stretch rolls before entering said bonding station, and wherein between 5 and 25% of the total stretching in the machine direction occurs in the last stretching step, which takes place between the last stretch roll and said bonding station, thereby forming a stretched film;
   laminating the stretched film and said at least two nonwoven webs in said bonding station by thermal bonding or ultrasonic welding in a bonding pattern comprising a plurality of bonding elements; and
   forming elongated apertures in said elastic film at or in close vicinity of at least some of the bonding elements, said elongated apertures being elongated in the machine direction and formed by rupture of said elastic film as a result of the stretching and laminating steps.

7. The method as claimed in claim 6, wherein said elastic film passes over at least three stretch rolls before entering said bonding station.

8. The method as claimed in claim 7, wherein said elastic film is stretched in at least three steps before entering said bonding station.

9. The method as claimed in claim 6, wherein the free length between adjacent stretch rolls is between 10 and 150 mm.

10. The method as claimed in claim 6, wherein the basis weight of the laminate is between 40 and 100 $g/m^2$ and the basis weight of the elastic film is between 20 and 60 $g/m^2$.

* * * * *